US005968965A

United States Patent [19]
Dinsmore et al.

[11] Patent Number: 5,968,965
[45] Date of Patent: *Oct. 19, 1999

[54] INHIBITORS OF FARNESYL-PROTEIN TRANSFERASE

[75] Inventors: Christopher J. Dinsmore, North Wales; George D. Hartman, Lansdale, both of Pa.

[73] Assignee: Merck & Co., Inc., Rahway, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/786,516

[22] Filed: Jan. 21, 1997

Related U.S. Application Data

[60] Provisional application No. 60/010,798, Jan. 30, 1996.
[51] Int. Cl.$^6$ ........................ A61K 31/415; C07D 233/64
[52] U.S. Cl. .................... 514/399; 548/336.5; 548/338.1
[58] Field of Search ............................. 548/338.1, 336.5; 514/399

[56] References Cited

U.S. PATENT DOCUMENTS

| | | |
|---|---|---|
| 5,130,317 | 7/1992 | Baader .................................. 514/256 |
| 5,141,851 | 8/1992 | Brown et al. . |
| 5,234,917 | 8/1993 | Finkelstein et al. . |
| 5,238,922 | 8/1993 | Graham et al. . |
| 5,326,773 | 7/1994 | Desolms et al. . |
| 5,340,828 | 8/1994 | Graham et al. . |
| 5,352,705 | 10/1994 | Deana et al. . |
| 5,439,918 | 8/1995 | Desolms et al. . |
| 5,468,733 | 11/1995 | Desolms et al. . |
| 5,480,893 | 1/1996 | Graham et al. . |
| 5,491,164 | 2/1996 | Desolms et al. . |
| 5,504,212 | 4/1996 | Desolms et al. . |
| 5,534,537 | 7/1996 | Ciccarone et al. . |
| 5,571,792 | 11/1996 | Bolton et al. . |
| 5,571,835 | 11/1996 | Anthony et al. . |
| 5,578,629 | 11/1996 | Ciccarone et al. . |
| 5,585,359 | 12/1996 | Breslin et al. . |

FOREIGN PATENT DOCUMENTS

| | | |
|---|---|---|
| 0 315 316 | 5/1989 | European Pat. Off. . |
| 0 387 431 | 9/1990 | European Pat. Off. . |
| WO 94/10138 | 5/1994 | WIPO . |
| WO 95/12612 | 5/1995 | WIPO . |
| WO 96/00736 | 1/1996 | WIPO . |
| WO 96/39137 | 12/1996 | WIPO . |
| WO 97/44350 | 11/1997 | WIPO . |

OTHER PUBLICATIONS

Aldrich Catalog P 478 # 22090–6 and 14183–6, 1996.
Lampe, J.W., et al., "Cardiotonic Agents. 6. Histamine Analogues as Potential Cardiovascular Selective H2 Agonists," J. Med. Chem., vol. 33, pp. 1688–1697 (1990).

Gibbs, J.B. et al., "Selective Inhibition of Farnesyl–Protein Transferase Blocks Ras Processing in Vivo," The Journal of Biological Chemistry, vol. 268, No. 11, pp. 7617–7620 (1993).

Goldstein, J.L. et al., "Nonfarnesylated Tetrapeptide Inhibitors of Protein Farnesyltransferase," Journal of Biological Chemistry, vol. 266, No. 24, pp. 15575–15578 (1991).

Graham, S.L., "Inhibitors of protein farnesylation: a new approach to cancer chemotherapy," Exp. Opin. Ther. Patents vol. 5 (12), pp. 1269–1285 (1995).

Kohl, N.E. et al., "Selective Inhibiton of ras–Dependent Transformation by a Farnesyltransferase Inhibitor", Science, vol. 260, pp. 1934–1937 (1993).

Kohl, N.E. et al., "Protein farnesyltransferase inhibitors block the growth of ras–dependent tumors in nude mice", Proc. Natl. Acad. Sci. USA, Med. Sciences, vol. 91, pp. 9141–9145 (1994).

Kohl, N.E., et al., "Inhibition of farnesyltransferse induces regression of mammary and salivary carcinomas in ras transgenic mice," Nature Medicine, vol. 1, No. 8, pp. 792–797 (1995).

Pompliano, D.L., "Steady–State Kinetic Mechanism of Ras Farnesyl:Protein Transferase," Biochemistry, vol. 31, pp. 3800–3807 (1992).

Sepp–Lorenzino, L., et al., "A Peptidomimetic Inhibitor of Farnesyl:Protein Transferase Blocks the Anchorage–dependent and–independent Growth of Human Tumor Cell Lines," Cancer Research, vol. 55, pp. 5302–5309 (1995).

James, G.L. et al., "Benzodiazepine Peptidomimetic BZA–5B Interrupts the MAP Kinase Activation Pathway in H–Ras–transformed Rat–1 Cells, but Not in Untransformed Cells," The Jour. of Biol. Chem., vol. 269, No. 44, pp. 27705–27714 (1994).

James, G.L. et al., "Benzodiazepine Peptidomimetics: Potent Inhibitors of Ras Farnesylation in Animal Cells", Science, vol. 260, pp. 1937–1942 (1993).

James, G.L., et al., "Polylysine and CVIM Sequences of K–RasB Dictate Specificity of Prenylation and Confer Resistance to Benzodiazepine Peptidomimetic in Vitro", The Jour. of Biol. Chem., vol. 270, No. 11, pp. 6221–6226 (1995).

*Primary Examiner*—Robert Gerstl
*Attorney, Agent, or Firm*—Dianne Pecoraro; David A. Muthard; Mark R. Daniel

[57] ABSTRACT

The present invention is directed to compounds which inhibit farnesyl-protein transferase (FTase) and the farnesylation of the oncogene protein Ras. The invention is further directed to chemotherapeutic compositions containing the compounds of this invention and methods for inhibiting farnesyl-protein transferase and the farnesylation of the oncogene protein Ras.

15 Claims, No Drawings

INHIBITORS OF FARNESYL-PROTEIN TRANSFERASE

This application is a provision of application Ser. No. 60/010,798, filed Jan. 30, 1996.

BACKGROUND OF THE INVENTION

The Ras proteins (Ha-Ras, Ki4a-Ras, Ki4b-Ras and N-Ras) are part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, *Ann. Rev. Biochem.* 62:851–891 (1993)). Mutated ras genes (Ha-ras, Ki4a-ras, Ki4b-ras and N-ras) are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., *Nature* 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., *Ann. Rev. Biochem.* 61:355–386 (1992); W. R. Schafer and J. Rine, *Ann. Rev. Genetics* 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., *J. Biol. Chem.* 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., *Science*, 260:1934–1937 (1993) and G. L. James et al., *Science*, 260:1937–1942 (1993). Recently, it has been shown that an inhibitor of farnesyl-protein transferase blocks the growth of ras-dependent tumors in nude mice (N. E. Kohl et al., *Proc. Natl. Acad. Sci U.S.A.*, 91:9141–9145 (1994) and induces regression of mammary and salivary carcinomas in ras transgenic mice (N. E. Kohl et al., *Nature Medicine*, 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., *Cell*, 62:81–88 (1990); Schaber et al., *J. Biol. Chem.*, 265:14701–14704 (1990); Schafer et al., *Science*, 249:1133–1139 (1990); Manne et al., *Proc. Natl. Acad. Sci USA*, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in two general classes. The first are analogs of farnesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., *PNAS*, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., *Science*, 260:1934–1937 (1993); Graham, et al., *J. Med. Chem.*, 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

It has recently been reported that farnesyl-protein transferase inhibitors are inhibitors of proliferation of vascular smooth muscle cells and are therefore useful in the prevention and thereapy of arteriosclerosis and diabetic disturbance of blood vessels (JP H7-112930).

It has recently been disclosed that certain tricyclic compounds which optionally incorporate a piperidine moiety are inhibitors of FPTase (WO 95/10514, WO 95/10515 and WO 95/10516). Imidazole-containing inhibitors of farnesyl protein transferase have also been disclosed (WO 95/09001 and EP 0 675 112 A1).

It is, therefore, an object of this invention to develop peptidomimetic compounds that do not have a thiol moiety, and that will inhibit farnesyl-protein transferase and thus, the post-translational farnesylation of proteins. It is a further object of this invention to develop chemotherapeutic compositions containing the compounds of this invention and methods for producing the compounds of this invention.

SUMMARY OF THE INVENTION

The present invention comprises small molecule peptidomimetic amide-containing compounds which inhibit the farnesyl-protein transferase. The instant compounds lack a thiol moiety and thus offer unique advantages in terms of improved pharmacokinetic behavior in animals, prevention of thiol-dependent chemical reactions, such as rapid autoxidation and disulfide formation with endogenous thiols, and reduced systemic toxicity. Further contained in this invention are chemotherapeutic compositions containing these farnesyl transferase inhibitors and methods for their production.

The compounds of this invention are illustrated by the formula I:

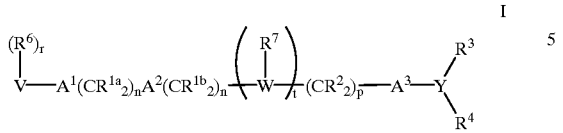

DETAILED DESCRIPTION OF THE INVENTION

The compounds of this invention are useful in the inhibition of farnesyl-protein transferase and the farnesylation of the oncogene protein Ras. In a first embodiment of this invention, the inhibitors of farnesyl-protein transferase are illustrated by the formula I:

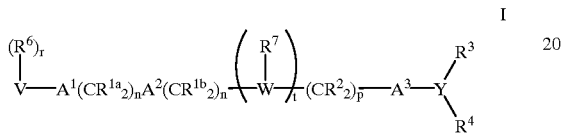

wherein:

$R^{1a}$, $R^{1b}$ and $R^2$ are independently selected from:
a) hydrogen,
b) aryl, heterocycle, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $NO_2$, $(R^8)_2N$—$C(NR^8)$—, $R^8C(O)$—, $R^8OC(O)$—, $N_3$, —$N(R^8)_2$, or $R^9OC(O)NR^8$—,
c) $C_1$–$C_6$ alkyl unsubstituted or substituted by aryl, heterocyclic, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $(R^8)_2N$— $C(NR^8)$—, $R^8C(O)$—, $R^8OC(O)$—, $N_3$, —$N(R^8)_2$, or $R^9OC(O)$—$NR^8$—;

$R^3$ and $R^4$ are independently selected from F, Cl, Br, $N(R^8)_2$, $CF_3$, $NO_2$, $(R^8)O$—, $(R^9)S(O)_m$—, $(R^8)C(O)NH$—, $H_2N$—$C(NH)$—, $(R^8)C(O)$—, $(R^8)OC(O)$—, $N_3$, CN, $CF_3(CH_2)_nO$—, $(R^9)OC(O)NR^8$—, $C_1$–$C_{20}$ alkyl, substituted or unsubstituted aryl and substituted or unsubstituted heterocycle;

$R^5$ is selected from:
a) hydrogen,
b) unsubstituted or substituted aryl,
c) unsubstituted or substituted heterocyclic,
d) unsubstituted or substituted $C_3$–$C_{10}$ cycloalkyl, and
e) $C_1$–$C_6$ alkyl substituted with hydrogen or a group selected from unsubstituted or substituted aryl, unsubstituted or substituted heterocyclic, unsubstituted or substituted $C_3$–$C_{10}$ cycloalkyl, $N(R^8)_2$, $CF_3$, $NO_2$, $(R^8)O$—, $(R^9)S(O)_m$—, $(R^8)C(O)NH$—, $H_2N$—$C(NH)$—, $(R^8)C(O)$—, $(R^8)OC(O)$—, $N_3$, CN $(R^9)OC(O)NR^8$—;

$R^6$ is independently selected from:
a) hydrogen,
b) aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, CN, $NO_2$, $R^8_2N$—C$(NR^8)$—, $R^8C(O)$—, $R^8OC(O)$—, $N_3$, —$N(R^8)_2$, or $R^9OC(O)NR^8$—, and
c) $C_1$–$C_6$ alkyl unsubstituted or substituted by aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NH$—, CN, $H_2N$—$C(NH)$—, $R^8C(O)$—, $R^8OC(O)$—, $N_3$, —$N(R^8)_2$, or $R^8OC(O)NH$—;

$R^7$ is selected from:
a) hydrogen,
b) $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, CN, $NO_2$, $(R^8)_2N$—C—$(NR^8)$—, $R^8C(O)$—, $R^8OC(O)$—, $N_3$, —$N(R^8)_2$, or $R^9OC(O)NR^8$—, and
c) $C_1$–$C_6$ alkyl unsubstituted or substituted by perfluoroalkyl, F, Cl, Br, $R^8O$—, $R^9S(O)_m$—, $R^8C(O)NR^8$—, CN, $(R^8)_2N$— $C(NR^8)$—, $R^8C(O)$—, $R^8OC(O)$—, $N_3$, —$N(R^8)_2$, or $R^9OC(O)NR^8$—;

$R^8$ is independently selected from hydrogen, $C_1$–$C_6$ alkyl, benzyl and aryl;

$R^9$ is independently selected from $C_1$–$C_6$ alkyl and aryl;

$A^1$ and $A^2$ are independently selected from: a bond, —CH=CH—, —C≡C—, —C(O)—, —C(O)$NR^8$—, —$NR^8C(O)$—, O, —$N(R^8)$—, —$S(O)_2N(R^8)$—, —$N(R^8)S(O)_2$—, or $S(O)_m$;

$A^3$ is selected from: —$NR^5C(O)$— or —C(O)NH—;

V is selected from:
a) hydrogen,
b) heterocycle,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

W is a heterocycle;

Y is aryl or heteroaryl;

m is 0, 1 or 2;

n is 0, 1, 2, 3 or 4;

p is 0, 1, 2, 3 or 4;

r is 0 to 5, provided that r is 0 when V is hydrogen; and t is 0 or 1;

or the pharmaceutically acceptable salts thereof.

A preferred embodiment of the compounds of this invention are illustrated by the formula Ia:

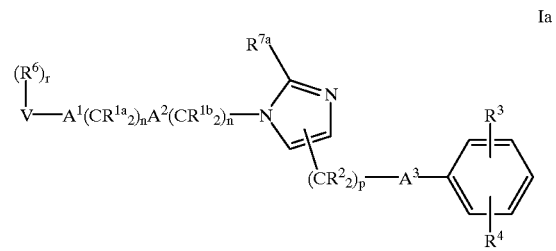

wherein:

$R^{1a}$ and $R^{1b}$ are independently selected from: hydrogen or $C_1$–$C_6$ alkyl;

$R^2$ is independently selected from:
a) hydrogen,
b) aryl, heterocycle, cycloalkyl, $R^8O$—, —$N(R^8)_2$ or $C_2$–$C_6$ alkenyl,
c) $C_1$–$C_6$ alkyl unsubstituted or substituted by aryl, heterocycle, cycloalkyl, alkenyl, $R^8O$—, or —$N(R^8)_2$;

$R^3$ and $R^4$ are independently selected from F, Cl, Br, $N(R^8)_2$, $CF_3$, $NO_2$, $(R^8)O$—, $(R^9)S(O)_m$—, $(R^8)C(O)$NH—, $H_2N$— $C(NH)$—, $(R^8)C(O)$—, $(R^8)OC(O)$—, $N_3$, CN, $(R^9)OC(O)NR^8$—, $C_1$–$C_{20}$ alkyl, substituted or unsubstituted aryl and substituted or unsubstituted heterocycle;

$R^5$ is selected from:
a) hydrogen, and
b) $C_1$–$C_6$ alkyl substituted with hydrogen or a group selected from unsubstituted or substituted aryl, unsubstituted or substituted heterocyclic, unsubstituted or substituted $C_3$–$C_{10}$ cycloalkyl, $N(R^8)_2$, $CF_3$, $NO_2$, $(R^8)O$—, $(R^9)S(O)_m$—, $(R^8)C(O)NH$—, $H_2N$—$C(NH)$—, $(R^8)C(O)$—, $(R^8)OC(O)$—, $N_3$, CN $(R^9)OC(O)NR^8$—;

$R^6$ is independently selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, $R^8OC(O)$—, —$N(R^8)_2$, or $R^9OC(O)NR^8$—, and
c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, $R^8OC(O)$—, —$N(R^8)_2$, or $R^9OC(O)NR^8$—;

$R^{7a}$ is hydrogen or methyl;
$R^8$ is independently selected from hydrogen, $C_1$–$C_6$ alkyl, benzyl and aryl;
$R^9$ is independently selected from $C_1$–$C_6$ alkyl and aryl;
$A^1$ and $A^2$ are independently selected from: a bond, —CH=CH—, —C≡C—, —C(O)—, —C(O)NR^8—, O, —N(R^8)—, or S(O)_m;
$A^3$ is selected from: —$NR^5C(O)$— or —$C(O)NH$—;
V is selected from:
a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

m is 0, 1 or 2;
n is 0, 1, 2, 3 or 4;
p is 0, 1, 2, 3 or 4; and
r is 0 to 5, provided that r is 0 when V is hydrogen;
or the pharmaceutically acceptable salts thereof.

A second preferred embodiment of the compounds of this invention are illustrated by the formula Ic:

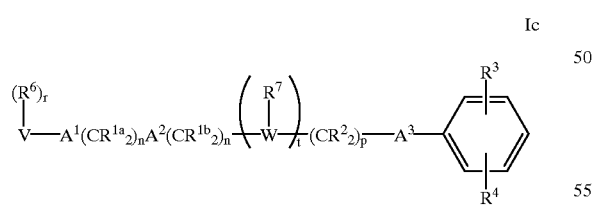

Ic wherein:
$R^{1a}$ and $R^{1b}$ are independently selected from: hydrogen or $C_1$–$C_6$ alkyl;
$R^2$ is independently selected from:
a) hydrogen,
b) aryl, heterocycle, cycloalkyl, $R^8O$—, —$N(R^8)_2$ or $C_2$–$C_6$ alkenyl,
c) $C_1$–$C_6$ alkyl unsubstituted or substituted by aryl, heterocycle, cycloalkyl, alkenyl, $R^8O$—, or —$N(R^8)_2$;

$R^3$ and $R^4$ are independently selected from F, Cl, Br, $N(R^8)_2$, $CF_3$, $NO_2$, $(R^8)O$—, $(R^9)S(O)_m$—, $(R^8)C(O)NH$—, $H_2N$—$C(NH)$—, $(R^8)C(O)$—, $(R^8)OC(O)$—, $N_3$, CN, $(R^9)OC(O)NR^8$—, $C_1$–$C_{20}$ alkyl, substituted or unsubstituted aryl and substituted or unsubstituted heterocycle;

$R^5$ is selected from:
a) hydrogen, and
b) $C_1$–$C_6$ alkyl substituted with hydrogen or a group selected from unsubstituted or substituted aryl, unsubstituted or substituted heterocyclic, unsubstituted or substituted $C_3$–$C_{10}$ cycloalkyl, $N(R^8)_2$, $CF_3$, $NO_2$, $(R^8)O$—, $(R^9)S(O)_m$—, $(R^8)C(O)NH$—, $H_2N$—$C(NH)$—, $(R^8)C(O)$—, $(R^8)OC(O)$—, $N_3$, CN $(R^9)OC(O)NR^8$—;

$R^6$ is independently selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, $R^8OC(O)$—, —$N(R^8)_2$, or $R^9OC(O)NR^8$—, and
c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, $R^8OC(O)$—, —$N(R^8)_2$, or $R^9OC(O)NR^8$—;

$R^7$ is selected from: hydrogen and $C_1$–$C_6$ alkyl;
$R^8$ is independently selected from hydrogen, $C_1$–$C_6$ alkyl, benzyl and aryl;
$R^9$ is independently selected from $C_1$–$C_6$ alkyl and aryl;
$A^1$ and $A^2$ are independently selected from: a bond, —CH=CH—, —C≡C—, —C(O)—, —C(O)NR^8—, O, —N(R^8)—, or S(O)_m;
$A^3$ is selected from: —$NR^5C(O)$— or —$C(O)NH$—;
V is selected from:
a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, and
provided that V is not hydrogen if $A^1$ is $S(O)_m$ and V is not hydrogen if $A^1$ is a bond, n is 0 and $A^2$ is $S(O)_m$;
W is a heterocycle selected from pyrrolidinyl, pyridinyl, thiazolyl, pyridonyl, 2-oxopiperidinyl, indolyl, quinolinyl, or isoquinolinyl;
m is 0, 1 or 2;
n is 0, 1, 2, 3 or 4;
p is 0, 1, 2, 3 or 4;
r is 0 to 5, provided that r is 0 when V is hydrogen; and
t is 1;
or the pharmaceutically acceptable salts thereof.

In a more preferred embodiment of this invention, the inhibitors of farnesyl-protein transferase are illustrated by the formula Ic:

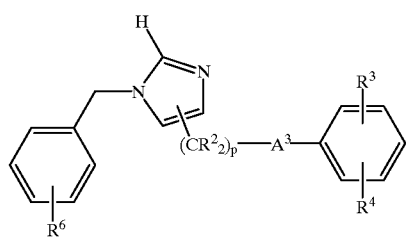

Ic wherein:

$R^{1b}$ is independently selected from:
a) hydrogen,
b) aryl, heterocycle, cycloalkyl, $R^8O—$, $—N(R^8)_2$ or $C_2-C_6$ alkenyl,
c) $C_1-C_6$ alkyl unsubstituted or substituted by aryl, heterocycle, cycloalkyl, alkenyl, $R^8O—$, or $—N(R^8)_2$;

$R^2$ are independently selected from: hydrogen or $C_1-C_6$ alkyl;

$R^3$ and $R^4$ are independently selected from F, Cl, Br, $N(R^8)_2$, $CF_3$, $NO_2$, $(R^8)O—$, $(R^9)S(O)_m—$, $(R^8)C(O)NH—$, $H_2N—C(NH)—$, $(R^8)C(O)—$, $(R^8)OC(O)—$, $N_3$, CN, $(R^9)OC(O)NR^8—$, $C_1-C_{20}$ alkyl, substituted or unsubstituted aryl and substituted or unsubstituted heterocycle;

$R^5$ is selected from:
a) hydrogen, and
b) $C_1-C_6$ alkyl substituted with hydrogen or a group selected from unsubstituted or substituted aryl, unsubstituted or substituted heterocyclic, unsubstituted or substituted $C_3-C_{10}$ cycloalkyl, $N(R^8)_2$, $CF_3$, $NO_2$, $(R^8)O—$, $(R^9)S(O)_m—$, $(R^8)C(O)NH—$, $H_2N—C(NH)—$, $(R^8)C(O)—$, $(R^8)OC(O)—$, $N_3$, CN $(R^9)OC(O)NR^8—$;

$R^6$ is independently selected from:
a) hydrogen,
b) $C_1-C_6$ alkyl, $C_2-C_6$ alkenyl, $C_2-C_6$ alkynyl, $C_1-C_6$ perfluoroalkyl, F, Cl, $R^8O—$, $R^8C(O)NR^8—$, CN, $NO_2$, $(R^8)_2N—C(NR^8)—$, $R^8C(O)—$, $R^8OC(O)—$, $—N(R^8)_2$, or $R^9OC(O)NR^8—$, and
c) $C_1-C_6$ alkyl substituted by $C_1-C_6$ perfluoroalkyl, $R^8O—$, $R^8C(O)NR^8—$, $(R^8)_2N—C(NR^8)—$, $R^8C(O)—$, $R^8OC(O)—$, $—N(R^8)_2$, or $R^9OC(O)NR^8—$;

$R^8$ is independently selected from hydrogen, $C_1-C_6$ alkyl, benzyl and aryl;

$R^9$ is independently selected from $C_1-C_6$ alkyl and aryl;

$A^3$ is selected from: $—NR^5C(O)—$ or $—C(O)NH—$;

m is 0, 1 or 2; and p is 0, 1, 2, 3 or 4;

or the pharmaceutically acceptable salts thereof.

In a second more preferred embodiment of this invention, the inhibitors of farnesyl-protein transferase are illustrated by the formula Id:

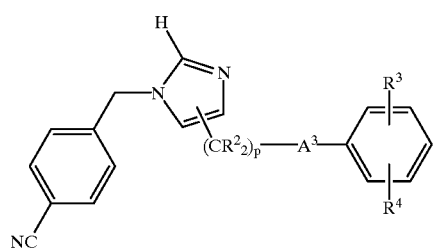

Id wherein:

$R^{1b}$ is independently selected from:
a) hydrogen,
b) aryl, heterocycle, cycloalkyl, $R^8O—$, $—N(R^8)_2$ or $C_2-C_6$ alkenyl,
c) $C_1-C_6$ alkyl unsubstituted or substituted by aryl, heterocycle, cycloalkyl, alkenyl, $R^8O—$, or $—N(R^8)_2$;

$R^2$ are independently selected from: hydrogen or $C_1-C_6$ alkyl;

$R^3$ and $R^4$ are independently selected from F, Cl, Br, $N(R^8)_2$, $CF_3$, $NO_2$, $(R^8)O—$, $(R^9)S(O)_m—$, $(R^8)C(O)NH—$, $H_2N—C(NH)—$, $(R^8)C(O)—$, $(R^8)OC(O)—$, $N_3$, CN, $(R^9)OC(O)NR^8—$, $C_1-C_{20}$ alkyl, substituted or unsubstituted aryl and substituted or unsubstituted heterocycle;

$R^5$ is selected from:
a) hydrogen, and
b) $C_1-C_6$ alkyl substituted with hydrogen or a group selected from unsubstituted or substituted aryl, unsubstituted or substituted heterocyclic, unsubstituted or substituted $C_3-C_{10}$ cycloalkyl, $N(R^8)_2$, $CF_3$, $NO_2$, $(R^8)O—$, $(R^9)S(O)_m—$, $(R^8)C(O)NH—$, $H_2N—C(NH)—$, $(R^8)C(O)—$, $(R^8)OC(O)—$, $N_3$, CN $(R^9)OC(O)NR^8—$;

$R^8$ is independently selected from hydrogen, $C_1-C_6$ alkyl, benzyl and aryl;

$R^9$ is independently selected from $C_1-C_6$ alkyl and aryl;

$A^3$ is selected from: $—NR^5C(O)—$ or $—C(O)NH—$;

m is 0, 1 or 2; and p is 0, 1, 2, 3 or 4;

or the pharmaceutically acceptable salts thereof.

Specific examples of the compounds of the invention are:

N-(3-chlorophenyl)-3-[1-(4-cyanobenzyl)-5-imidazolyl] propionamide hydrochloride (1)

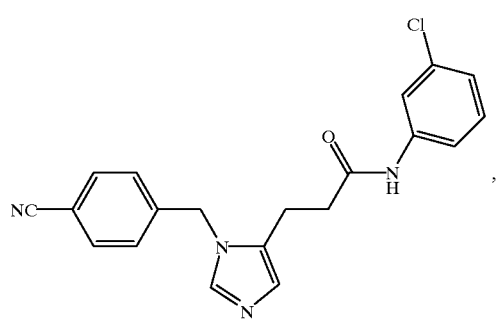

or the pharmaceutically acceptable salts thereof.

The compounds of the present invention may have asymmetric centers and occur as racemates, racemic mixtures, and as individual diastereomers, with all possible isomers, including optical isomers, being included in the present invention. When any variable (e.g. aryl, heterocycle, $R^{1a}$, $R^2$ etc.) occurs more than one time in any constituent, its definition on each occurence is independent at every other occurence. Also, combinations of substituents/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge. "Halogen" or "halo" as used herein means fluoro, chloro, bromo and iodo.

As used herein, "aryl" is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

The term heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, and thienyl.

As used herein, the terms "substituted aryl", "substituted heterocycle" and "substituted cycloalkyl" are intended to include the cyclic group which is substituted with 1 or 2 substitutents selected from the group which includes but is not limited to F, Cl, Br, $CF_3$, $NH_2$, $N(C_1-C_6 \text{ alkyl})_2$, $NO_2$, CN, $(C_1-C_6 \text{ alkyl})O$—, —OH, $(C_1-C_6 \text{ alkyl})S(O)_m$—, $(C_1-C_6 \text{ alkyl})C(O)NH$—, $H_2N$—C(NH)—, $(C_1-C_6 \text{ alkyl})C(O)$—, $(C_1-C_6 \text{ alkyl})OC(O)$—, $N_3$, $(C_1-C_6 \text{ alkyl})OC(O)NH$— and $C_1-C_{20}$ alkyl.

Lines drawn into the ring systems from substituents (such as from $R^3$, $R^4$ etc.) indicate that the bond may be attached to any of the substitutable ring carbon atoms.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

It is intended that the definition of any substituent or variable (e.g., $R^{1a}$, n, etc.) at a particular location in a molecule be independent of its definitions elsewhere in that molecule. Thus, $-N(R^8)_2$ represents —NHH, $-NHCH_3$, $-NHC_2H_5$, etc. It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

Preferably, $R^{1a}$, $R^{1b}$ and $R^2$ are independently selected from: hydrogen, $-N(R^8)_2$, $R^8C(O)NR^8$— or $C_1-C_6$ alkyl unsubstituted or substituted by $-N(R^8)_2$, $R^8O$— or $R^8C(O)NR^8$—.

Preferably, $R^3$ and $R^4$ are independently selected from: hydrogen, perfluoroalkyl, F, Cl, Br, $R^8O$—, $R^9S(O)_m$—, CN, $NO_2$, $R^8_2N$—$C(NR^8)$—, $R^8C(O)$—, $R^8OC(O)$—, $N_3$, $-N(R^8)_2$, or $R^9OC(O)NR^8$— and $C_1-C_6$ alkyl.

Preferably, $R^5$ is hydrogen or $C_1-C_6$ alkyl substituted with hydrogen, $R^9S(O)_m$—, $CF_3$— or an unsubstituted or substituted aryl group.

Preferably, $R^6$ is selected from: hydrogen, perfluoroalkyl, F, Cl, Br, $R^8O$—, $R^9S(O)_m$—, CN, $NO_2$, $R^8_2N$—$C(NR^8)$—, $R^8C(O)$—, $R^8OC(O)$—, $N_3$, $-N(R^8)_2$, or $R^9OC(O)NR^8$— and $C_1-C_6$ alkyl.

Preferably, $R^7$ is hydrogen or methyl. Most preferably, $R^7$ is hydrogen.

Preferably, $R^8$ is selected from H, $C_1-C_6$ alkyl and benzyl.

Preferably, $A^1$ and $A^2$ are independently selected from: a bond, $-C(O)NR^8$—, $-NR^8C(O)$—, O, $-N(R^8)$—, $-S(O)_2N(R^8)$— and $-N(R^8)S(O)_2$—.

Preferably, V is selected from hydrogen, heterocycle and aryl. More preferably, V is phenyl.

Preferably, Y is selected from phenyl, pyridyl, furanyl and thienyl. More preferably, Y is phenyl.

Preferably, n and r are independently 0, 1, or 2.

Preferably p is 1, 2 or 3.

Preferably t is 1.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Reactions used to generate the compounds of this invention are prepared by employing reactions as shown in Schemes 1–12, in addition to other standard manipulations such as ester hydrolysis, cleavage of protecting groups, etc., as may be known in the literature or exemplified in the experimental procedures. Substituents R' and R'CH$_2$—, as shown in the Schemes, represent the substituents R$^8$, R$^9$ and others, depending on the compound of the instant invention that is being synthesized.

These reactions may be employed in a linear sequence to provide the compounds of the invention or they may be used to synthesize fragments which are subsequently joined by the alkylation reactions described in the Schemes.

Synopsis of Schemes 1–12:

The requisite intermediates are in some cases commercially available, or can be prepared according to literature procedures, for the most part. Scheme 1 illustrates the synthesis of one of the preferred embodiments of the instant invention, wherein the variable W is present as a imidazolyl moiety that is substituted with a suitably substituted benzyl group. Substituted protected imidazole alkanols II can be prepared by methods known in the art, such as those described by F. Schneider, *Z. Physiol. Chem.*, 3:206–210 (1961) and C. P. Stewart, *Biochem. Journal*, 17:130–133 (1923). Intermediate II can then be oxidized to the imidazole alkanoic acid by methods known in the art. Some imidazole alkanoic acids containing alkyl substituents on the carbon atoms of the imidazole ring can be prepared by hydrolysis of the corresponding nitrites, which can be prepared by methods known in the art (see for example: *J. Med. Chem.*, 19:923 (1976)).

Benzylation and deprotection of the imidazole alkanoate ester provides intermediate IV which can be hydrolyzed to the acid V and coupled to a suitably substituted analine VI to provide the instant compound VII.

Schemes 2–5 illustrate syntheses of other suitably substituted alkanoate esters useful in the syntheses of the instant compounds wherein the variable W is present as a pyridyl moiety. Similar synthetic strategies for preparing ester intermediates that incorporate other heterocyclic moieties for variable W are also well known in the art.

The suitably substituted aniline V can be reacted with a variety of other carboxylic acids, such as VIII, as illustrated in Scheme 6. The product IX can be deprotected to give the instant compound X. The product X is isolated in the salt form, for example, as a trifluoroacetate, hydrochloride or acetate salt, among others. The product diamine X can further be selectively protected to obtain XI, which can subsequently be reductively alkylated with a suitable aldehyde, such as XII, to obtain XIII. Removal of the protecting group, and conversion to cyclized products such as the dihydroimidazole XIV can be accomplished by literature procedures.

If the aniline V is coupled to an acid which also has a protected hydroxyl group, such as XV in Scheme 7, the protecting groups can be subsequently removed to unmask the hydroxyl group (Schemes 7 and 8). The primary alcohol XVI can be oxidized under standard conditions to e.g. an aldehyde, which can then be reacted with a variety of organometallic reagents such as Grignard reagents, to obtain secondary alcohols such as XVIII. In addition, the fully deprotected amino alcohol XIX can be reductively alkylated (under conditions described previously) with a variety of aldehydes to obtain secondary amines, such as XXX (Scheme 8), or tertiary amines.

The Boc protected amino alcohol XVIa can also be utilized to synthesize aziridines such as XXI (Scheme 9). Treating XVIa with 1,1'-sulfonyldiimidazole and sodium hydride in a solvent such as dimethylformamide leads to the formation of aziridine XXI. The aziridine can be reacted in the presence of a nucleophile, such as a thiol, in the presence of base to yield the ring-opened product XXII, which can be deprotected to provide the instant compound.

In addition, the aniline V can be reacted with acids derived from amino acids such as O-alkylated tyrosines, according to standard procedures, to obtain compounds such as XXVI. When R' is an aryl group, XXVI can first be hydrogenated to unmask the phenol, and the amine group deprotected with acid to produce XXVII. Alternatively, the amine protecting group in XXVI can be removed, and O-alkylated phenolic amines such as XXVIII produced.

Schemes 11–12 illustrate the preparation of compounds of the instant invention wherein the orientation of the A$^3$ amide moiety is reversed relative to the compounds of Schemes 1–10. Thus the alkanol II may be protected and converted to the corresponding amine XXX via the azide, as shown in Scheme 11. Alternatively, if the appropriately substituted protected amine, such as a protected histamine XXXI, is available, that reagent may be ring alkylated to provide the intermediate amine XXXII.

As shown in Scheme 12, an amine such as intermediate XXX may be reacted with a suitably subsituted benzoic acid, such as compound XXXIII, to provide the instant compound XXXIV. The carbamate nitrogen of XXXIV may be subsequently alkylated as described previously in Scheme 1.

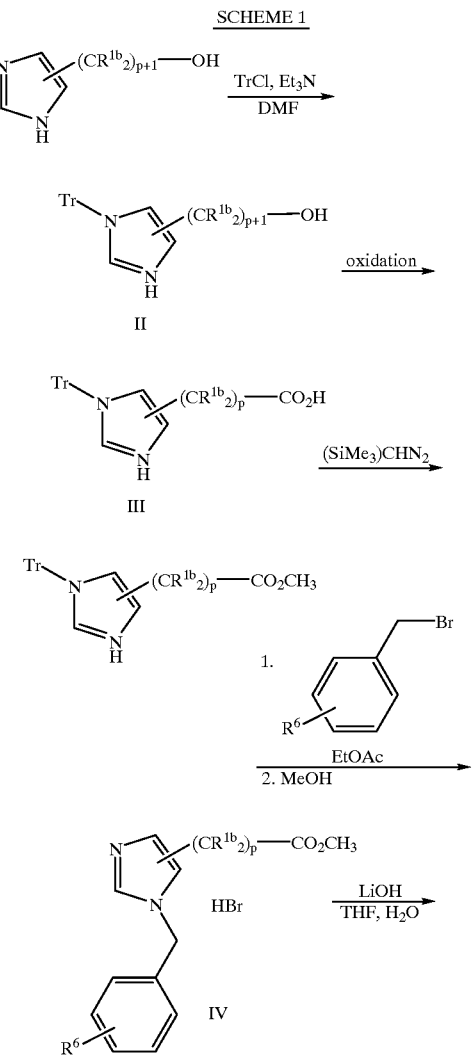

SCHEME 1

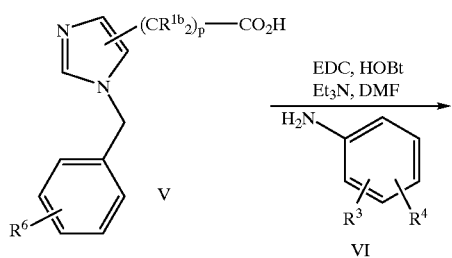
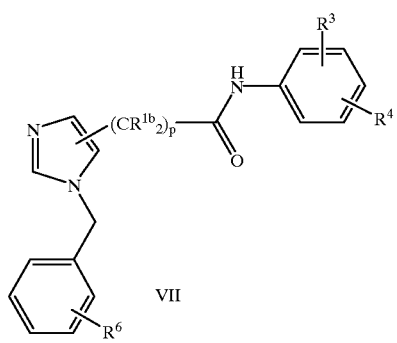
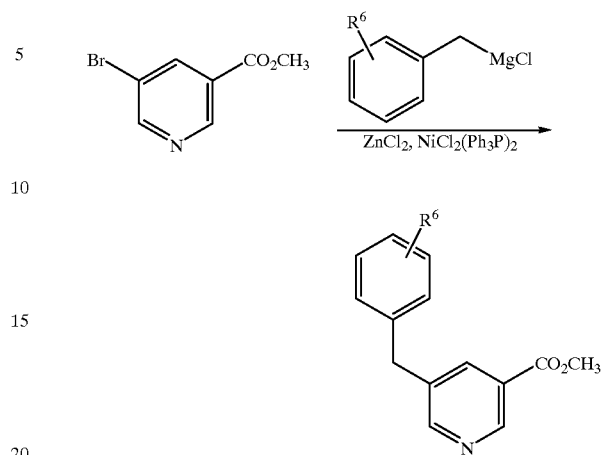
SCHEME 2
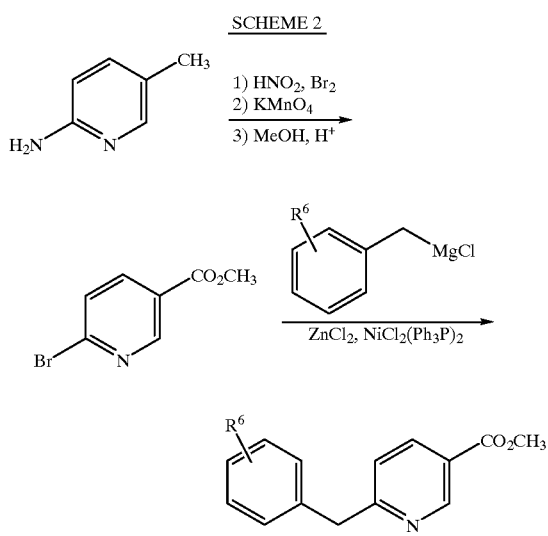
SCHEME 3
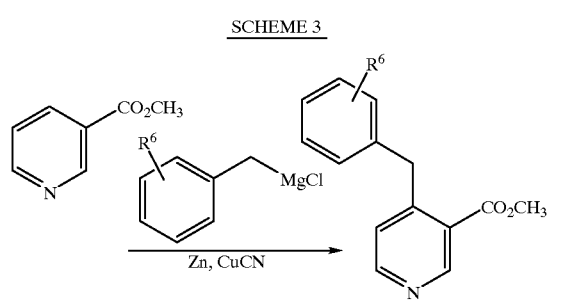
SCHEME 4
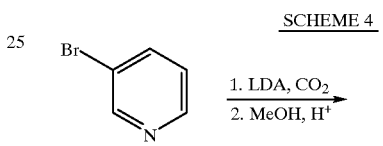
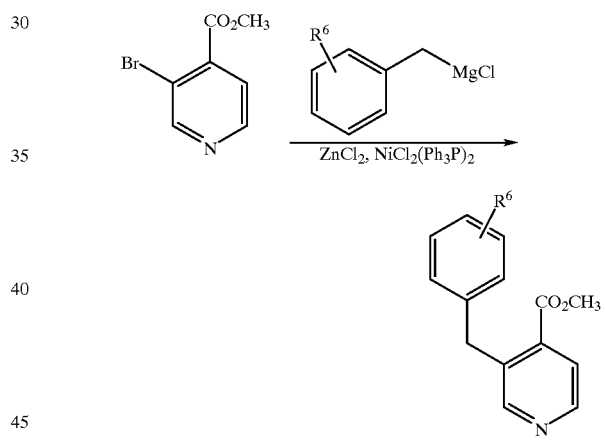
SCHEME 5

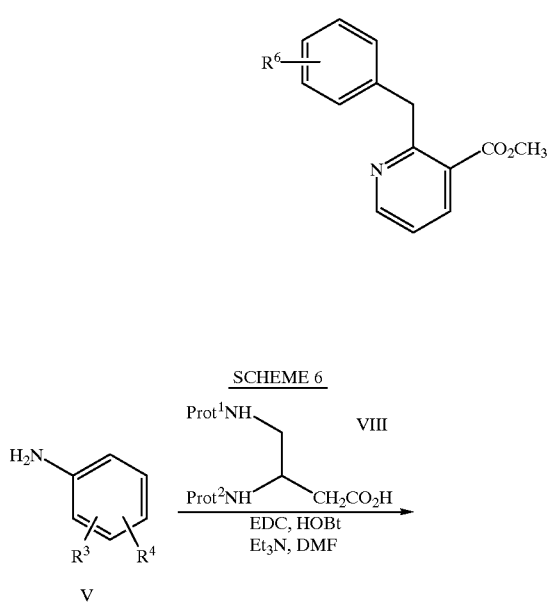
SCHEME 6
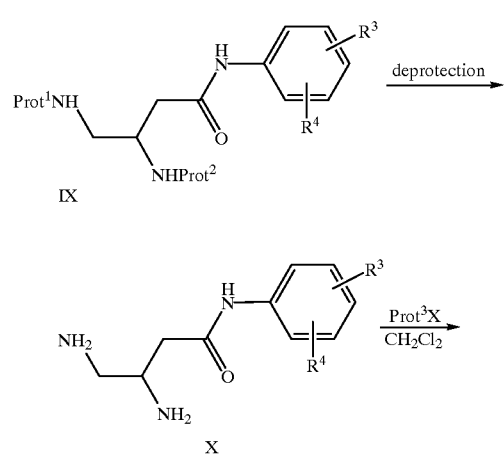
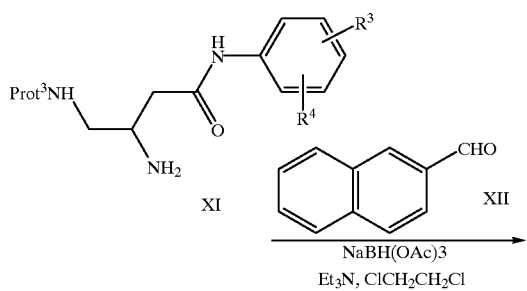
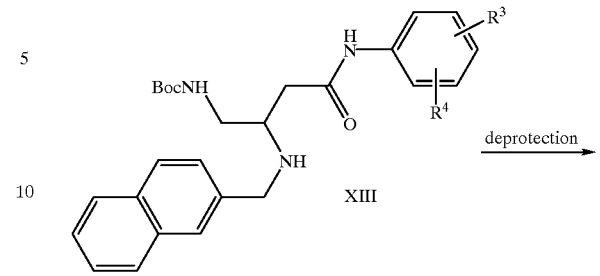
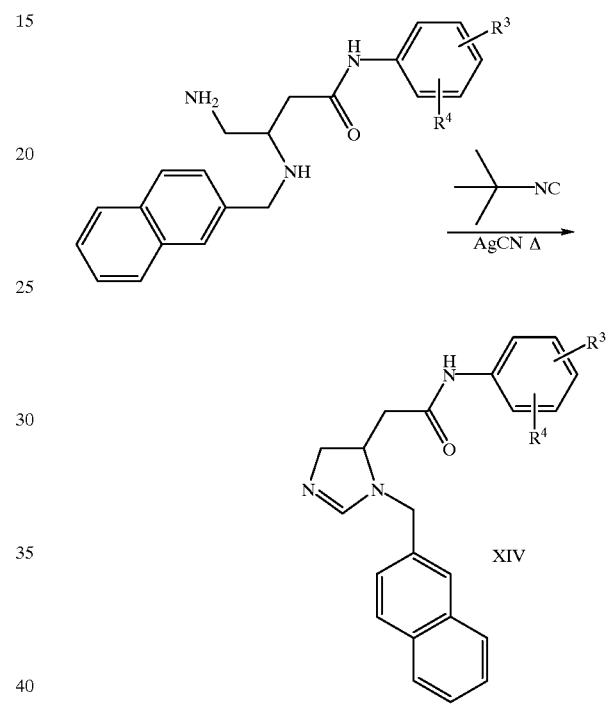
SCHEME 7
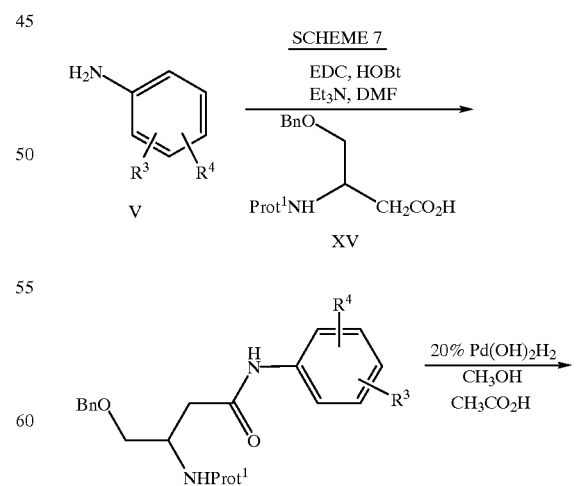

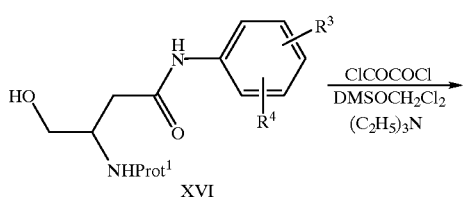
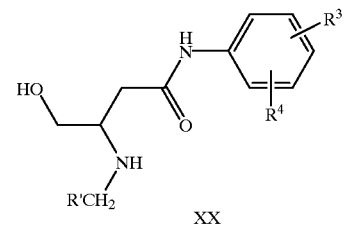
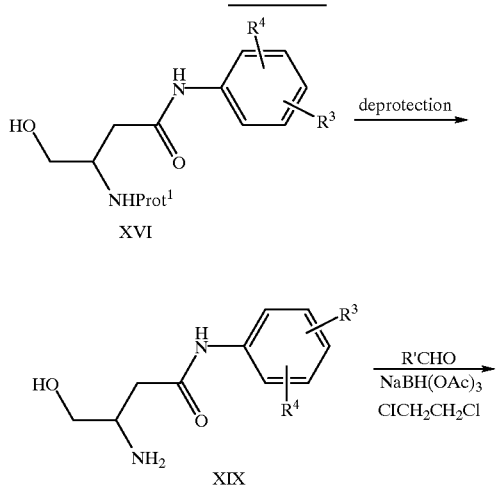
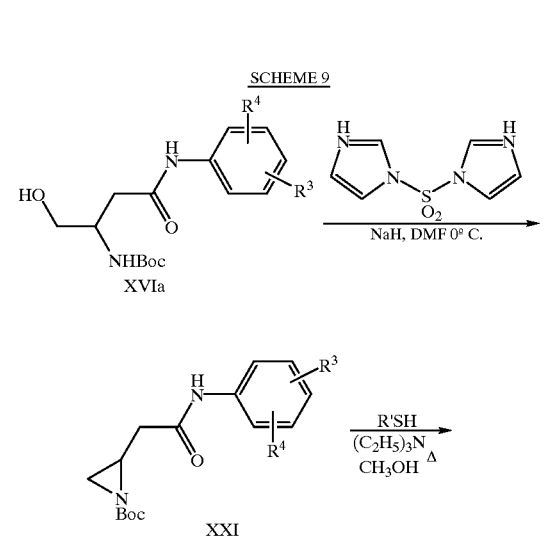

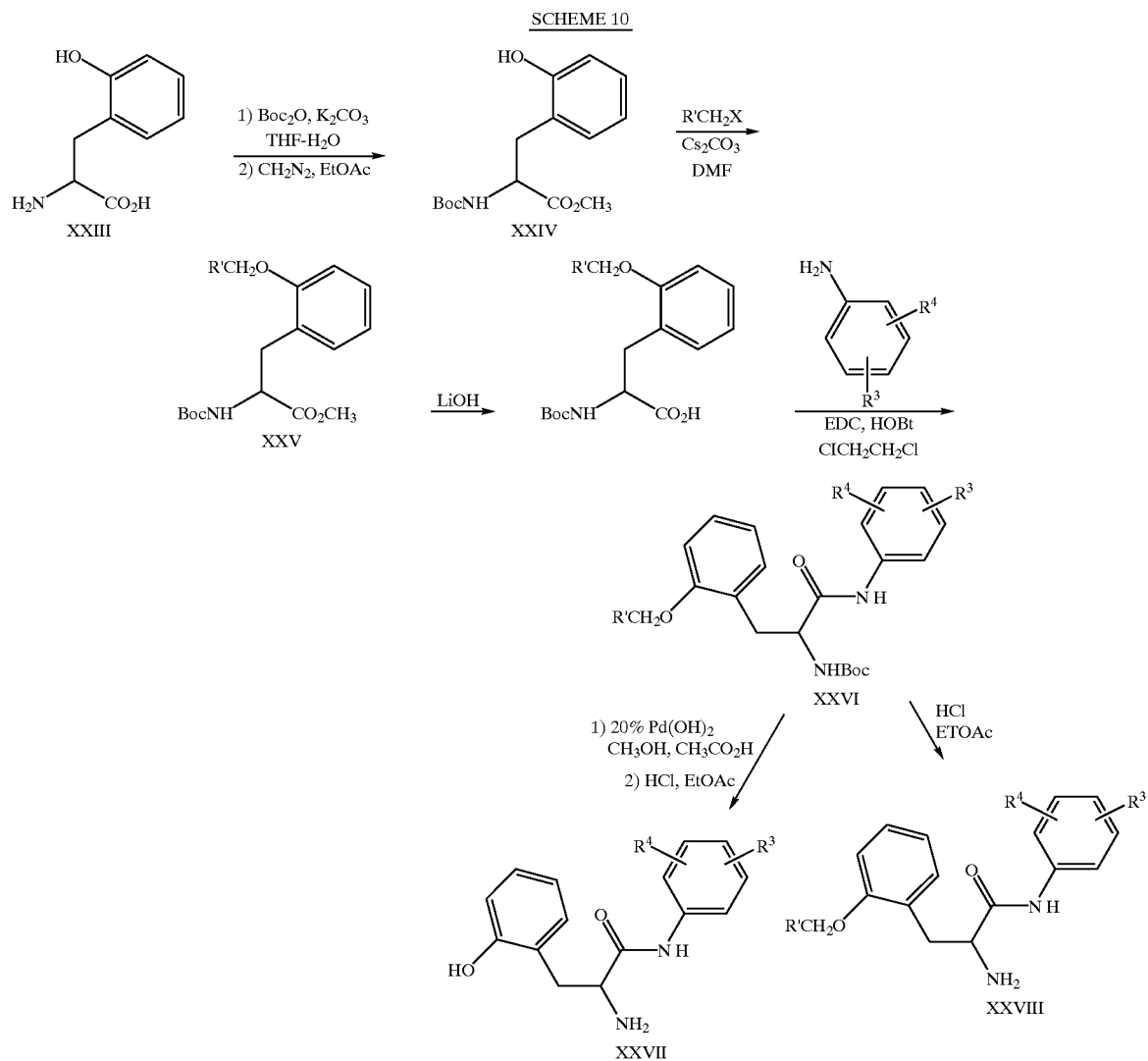
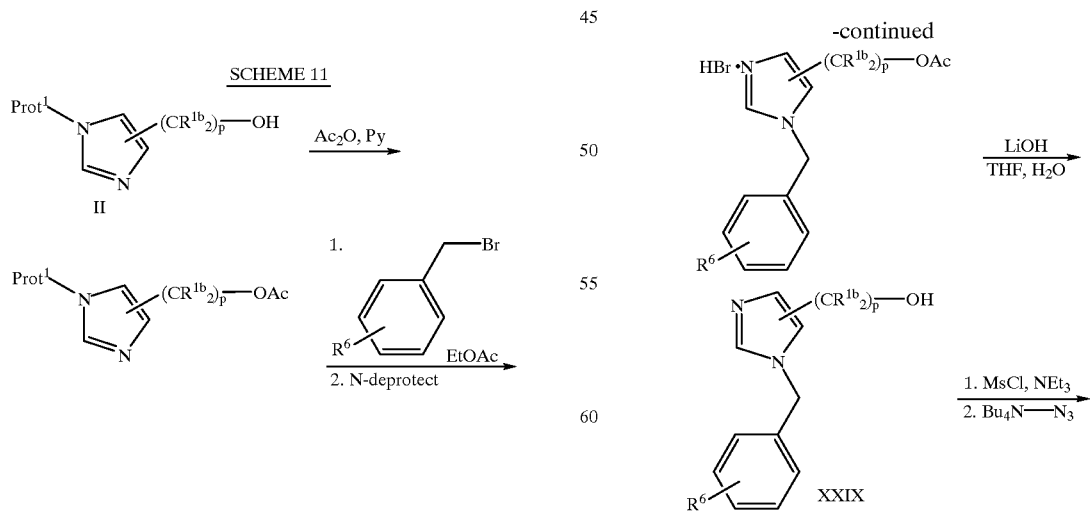

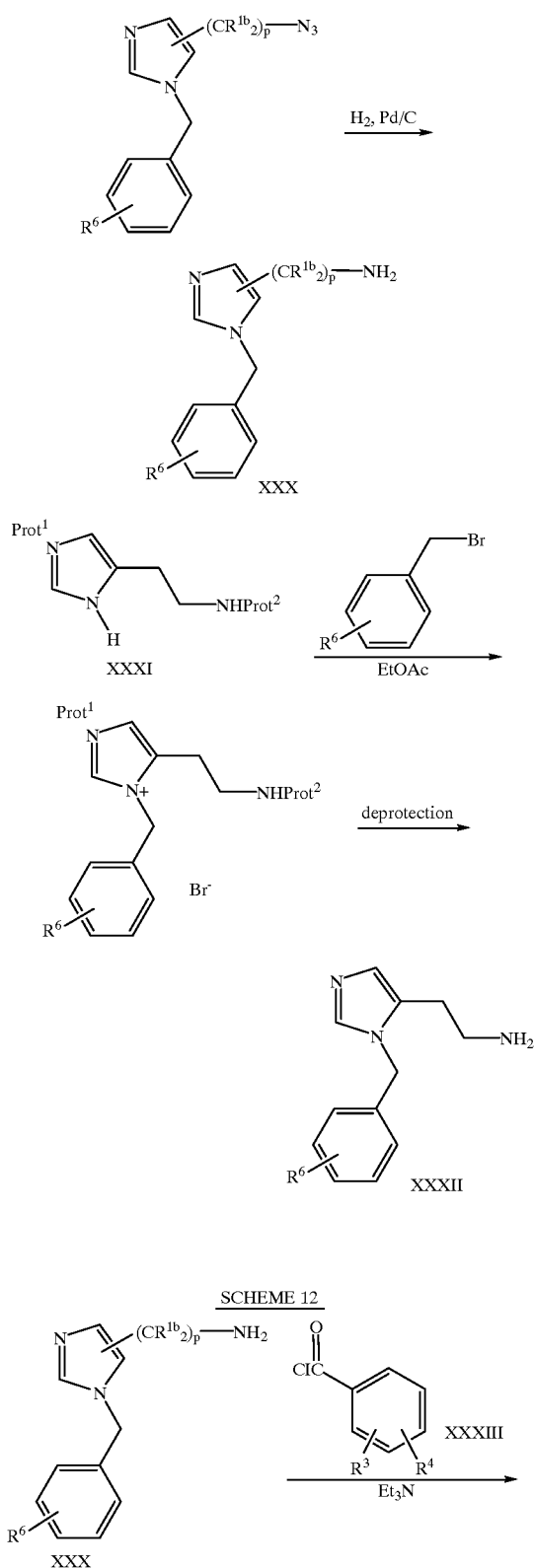

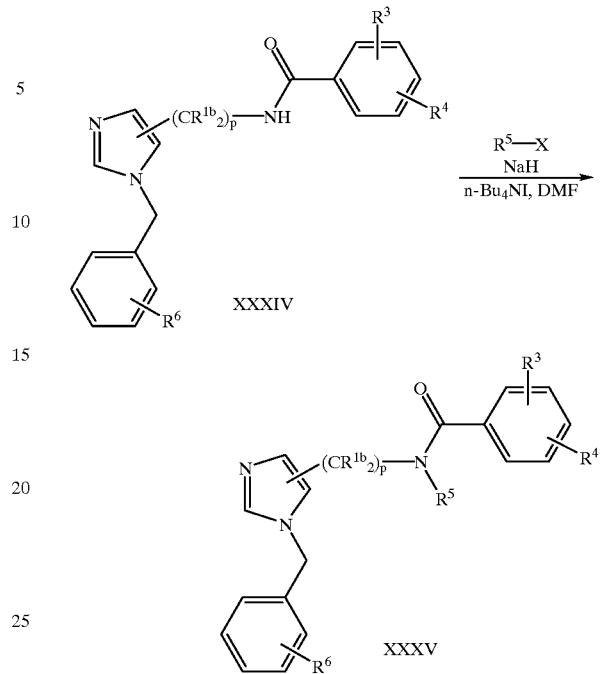

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras formation (i.e., neurofibromen (NF-1), neu, scr, ab1, lck, fyn) or by other mechanisms.

The compounds of the instant invention inhibit farnesyl-protein transferase and the farnesylation of the oncogene protein Ras. The instant compounds may also inhibit tumor angiogenisis, thereby affecting the growth of tumors (J. Rak et al. *Cancer Research*, 55:4575–4580 (1995)). Such anti-angiogenisis properties of the instant compounds may also be useful in the treatment of certain forms of blindness related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, a component of NF-1 is a benign proliferative disorder.

The instant compounds may also be useful in the treatment of certain viral infections, in particular in the treatment of hepatitis delta and related viruses (J. S. Glenn et al. *Science*, 256:1331–1333 (1992)).

The compounds of the instant invention are also useful in the prevention of restenosis after percutaneous transluminal coronary angioplasty by inhibiting neointimal formation (C. Indolfi et al. *Nature medicine*, 1:541–545(1995)).

The instant compounds may also be useful in the treatment and prevention of polycystic kidney disease (D. L. Schaffner et al. *American Journal of Pathology*, 142:1051–1060 (1993) and B. Cowley, Jr. et al. *FASEB Journal*, 2:A3160 (1988)).

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

Example 1

N-(3-chlorophenyl)-3-[1-(4-cyanobenzyl)-5-imidazolyl] propionamide hydrochloride (1)

Step 1: Preparation of methyl 3-(4-imidazolyl)-2-propenoate (2)

Through a suspension of urocanic acid (5.0 g) in methanol at 0° C. was bubbled HCl gas until the solution was saturated. The reaction was stirred for one hour, then concentrated in vacuo to dryness to provide the crude product 2 which was used in the next step without further purification.

Step 2: Preparation of methyl 3-(4-imidazolyl)propionate (3)

To a solution of ester 2 (5.3 g) in methanol at room temperature was added 10% palladium on carbon (20 mg) under a blanket of argon. A balloon of hydrogen was applied, and the reaction was stirred for one hour. The solution was filtered, and then concentrated in vacuo to dryness to provide the crude product 3 which was sufficiently pure for use in the next step.

Step 3: Preparation of methyl 3-(1-triphenylmethyl-4-imidazolyl)-propionate (4)

To a solution of ester 3 (1.77 g) in 10 mL of dry DMF at room temperature was added triethylamine (3.25 mL). A white solid precipitated from the solution. Chlorotriphenylmethane (2.65 g) in 12 mL of DMF was added dropwise. The reaction mixture was stirred for 20 hours, then poured into 40% EtOAc/hexane solution and washed with two portions of water. The organic layer was extracted with sat. aq. NaHCO$_3$ solution and brine, then dried (Na$_2$SO$_4$), filtered, and concentrated in vacuo to provide the crude product 4 which was sufficiently pure for use in the next step.

Step 4: Preparation of methyl 3-[1-(4-cyanobenzyl)-5-imidazolyl]propionate (5)

A solution of 4 (4.3 g) and α-bromo-p-tolunitrile (2.03 g) in 30 mL of EtOAc was stirred at 65° C. for 20 hours, during which a pale yellow precipitate formed. The reaction was cooled to room temperature, concentrated in vacuo, and dissolved in 30 mL of methanol. The resulting solution was warmed to 60° C. for one hour, then reconcentrated in vacuo.

The solid material was triturated to remove soluble materials, then taken up in $CH_2Cl_2$/50% aq. $NaHCO_3$ soln. The aqueous layer was extracted three times with $CH_2Cl_2$ and concentrated in vacuo to provide the crude product. Purification by silica gel chromatography (5% MeOH/$CH_2Cl_2$) gave the titled compound as a white waxy solid.

Step 5: Preparation of 3-[1-(4-cyanobenzyl)-5-imidazolyl]-propionic acid hydrochloride (6)

To a solution of the methyl ester 5 (1.10 g) in 10 mL of THF and 5 mL of water was added lithium hydroxide monohydrate (172 mg). After two hours, the reaction was cooled to 0° C., and a 1 M solution of HCl/ether (8.2 mL) was added. The solution was concentrated and dried in vacuo next to $P_2O_5$ to provide the product 6 as a white solid.

Step 6: Preparation of N-(3-chlorophenyl)-3-[1-(4-cyanobenzyl)-5-imidazolyl]propionamide hydrochloride (1)

To a 0° C. solution of acid 6 (141 mg) in 2 mL of dry DMF was added triethylamine (0.089 mL), and 3-chloroaniline (0.046 mL). 1-Hydroxybenzotriazole hydrate (80 mg) was added, followed by 1-ethyl-3-(3-dimethylaminopropyl) carbodiimide hydrochloride (106 mg). After six hours, the reaction was poured into EtOAc, washed with sat. aq. $NaHCO_3$ solution and brine, then dried ($Na_2SO_4$), filtered, and concentrated in vacuo to provide the crude product. Purification by silica gel chromatography (2–6% MeOH/$CH_2Cl_2$) gave a white foam which was taken up in $CH_2Cl_2$, treated with 1 M HCl/ether solution, and concentrated in vacuo. The product hydrochloride 1 was isolated as a white powder.

FAB mass spectrum m/e 365 (M+1). Analysis calculated for $C_{20}H_{17}ClN_4O \cdot 1.00$ $HCl \cdot 0.50$ $H_2O$: C, 58.55; H, 4.67; N, 13.65; Found: C, 58.61; H, 4.53; N, 13.47.

Example 2

In vitro Inhibition of Ras Farnesyl Transferase

Assays of farnesyl-protein transferase. Partially purified bovine FPTase and Ras peptides (Ras-CVLS, Ras-CVIM and Ras-CAIL) were prepared as described by Schaber et al., *J. Biol. Chem.* 265:14701–14704 (1990), Pompliano, et al., *Biochemistry* 31:3800 (1992) and Gibbs et al., *PNAS U.S.A.* 86:6630–6634 (1989), respectively. Bovine FPTase was assayed in a volume of 100 µl containing 100 mM N-(2-hydroxy ethyl) piperazine-N'-(2-ethane sulfonic acid) (HEPES), pH 7.4, 5 mM $MgCl_2$, 5 mM dithiothreitol (DTT), 100 mM [$^3$H]-farnesyl diphosphate ([$^3$H]-FPP; 740 CBq/mmol, New England Nuclear), 650 nM Ras-CVLS and 10 µg/ml FPTase at 31° C. for 60 min. Reactions were initiated with FPTase and stopped with 1 ml of 1.0 M HCL in ethanol. Precipitates were collected onto filter-mats using a TomTec Mach II cell harvestor, washed with 100% ethanol, dried and counted in an LKB β-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of radioactivity in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 µM $ZnCl_2$ and 100 nM Ras-CVIM were added to the reaction mixture. Reactions were performed for 30 min., stopped with 100 µl of 30% (v/v) trichloroacetic acid (TCA) in ethanol and processed as described above for the bovine enzyme.

The compound of the instant invention described in Example 1 was tested for inhibitory activity against human FPTase by the assay described above and was found to have $IC_{50}$ of <10 µM.

Example 3

In vivo Ras Farnesylation Assay

The cell line used in this assay is a v-ras line derived from either Rat1 or NIH3T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labelled in 3 ml methionine-free DMEM supplemeted with 10% regular DMEM, 2% fetal bovine serum and 400 mCi[$^{35}$S]methionine (1000 Ci/mmol). After an additional 20 hours, the cells are lysed in 1 ml lysis buffer (1% NP40/20 mM HEPES, pH 7.5/5 mM $MgCl_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., *J. Virol.* 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100. 0.5% deoxycholate/0.1%/SDS/0.1 M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

Example 4

In vivo Growth Inhibition Assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of 1×10$^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

What is claimed is:

1. A compound which inhibits farnesyl-protein transferase of the formula Ia:

Ia

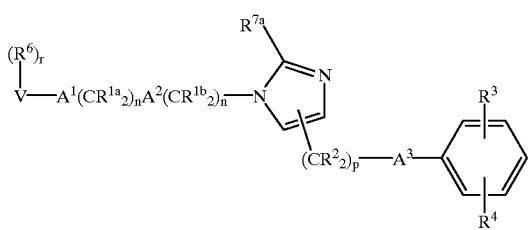

wherein:
$R^{1a}$ and $R^{1b}$ are independently selected from: hydrogen or $C_1$–$C_6$ alkyl;
$R^2$ is independently selected from:
  a) hydrogen,
  b) aryl, heterocycle, cycloalkyl, $R^8O$—, —$N(R^8)_2$ or $C_2$–$C_6$ alkenyl,
  c) $C_1$–$C_6$ alkyl unsubstituted or substituted by aryl, heterocycle, cycloalkyl, alkenyl, $R^8O$—, or —$N(R^8)_2$;
$R^3$ and $R^4$ are independently selected from: hydrogen, perfluoroalkyl, F, Cl, Br, $R^8O$—, $R^9S(O)_m$—, CN, $NO_2$, $R^8_2N$—$C(NR^8)$—, $R^8C(O)$—, $R^8OC(O)$—, $N_3$, —$N(R^8)_2$, or $R^9OC(O)NR^8$— and $C_1$–$C_6$ alkyl;
$R^5$ is selected from:
  a) hydrogen, and
  b) $C_1$–$C_6$ alkyl substituted with hydrogen or a group selected from unsubstituted or substituted aryl, unsubstituted or substituted heterocyclic, unsubstituted or substituted $C_3$–$C_{10}$ cycloalkyl, $N(R^8)_2$, $CF_3$, $NO_2$, $(R^8)O$—, $(R^9)S(O)_m$—, $(R^8)C(O)NH$—, $H_2N$—$C(NH)$—, $(R^8)C(O)$—, $(R^8)OC(O)$—, $N_3$, CN $(R^9)OC(O)NR^8$—;
$R^6$ is independently selected from:
  a) hydrogen,
  b) $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, $R^8OC(O)$—, —$N(R^8)_2$, or $R^9OC(O)NR^8$—, and
  c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, $R^8OC(O)$—, —$N(R^8)_2$, or $R^9OC(O)NR^8$—;
$R^{7a}$ is hydrogen or methyl;
$R^8$ is independently selected from hydrogen, $C_1$–$C_6$ alkyl, benzyl and aryl;
$R^9$ is independently selected from $C_1$–$C_6$ alkyl and aryl;
$A^1$ and $A^2$ are independently selected from: a bond, —CH=CH—, —C≡C—, —C(O)—, —C(O)$NR^8$—, O, —$N(R^8)$—, or $S(O)_m$;
$A^3$ is selected from: —$NR^5C(O)$— or —C(O)NH—;
V is selected from:
  a) heterocycle selected from pyrrolidinyl, imidazolyl, pyridinyl, thiazolyl, pyridonyl, 2-oxopiperidinyl, indolyl, quinolinyl, isoquinolinyl, and thienyl,
  b) aryl,
  c) $C_1$–$C_{20}$ alkyl wherein from 0 to 4 carbon atoms are replaced with a heteroatom selected from O, S, and N, and
  d) $C_2$–$C_{20}$ alkenyl, and
m is 0, 1, or 2;
n is 0, 1, 2, 3 or 4;
p is 0, 1, 2, 3 or 4; and
r is 0 to 5;

or an optical isomer or pharmaceutically acceptable salt thereof.

2. A compound which inhibits farnesyl-protein transferase of the formula Ib:

Ib

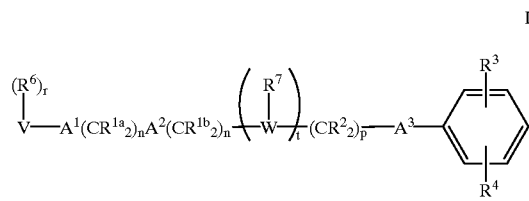

wherein:
$R^{1a}$ and $R^{1b}$ are independently selected from: hydrogen or $C_1$–$C_6$ alkyl;
$R^2$ is independently selected from:
  a) hydrogen,
  b) aryl, heterocycle, cycloalkyl, $R^8O$—, —$N(R^8)_2$ or $C_2$–$C_6$ alkenyl,
  c) $C_1$–$C_6$ alkyl unsubstituted or substituted by aryl, heterocycle, cycloalkyl, alkenyl, $R^8O$—, or —$N(R^8)_2$;
$R^3$ and $R^4$ are independently selected from: hydrogen, perfluoroalkyl, F, Cl, Br, $R^8O$—, $R^9S(O)_m$—, CN, $NO_2$, $R^8_2N$—$C(NR^8)$—, $R^8C(O)$—, $R^8OC(O)$—, $N_3$, —$N(R^8)_2$, or $R^9OC(O)NR^8$— and $C_1$–$C_6$ alkyl;
$R^5$ is selected from:
  a) hydrogen, and
  b) $C_1$–$C_6$ alkyl substituted with hydrogen or a group selected from unsubstituted or substituted aryl, unsubstituted or substituted heterocyclic, unsubstituted or substituted $C_3$–$C_{10}$ cycloalkyl, $N(R^8)_2$, $CF_3$, $NO_2$, $(R^8)O$—, $(R^9)S(O)_m$—, $(R^8)C(O)NH$—, $H_2N$—$C(NH)$—, $(R^8)C(O)$—, $(R^8)OC(O)$—, $N_3$, CN $(R^9)OC(O)NR^8$—;
$R^6$ is independently selected from:
  a) hydrogen,
  b) $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, $R^8OC(O)$—, —$N(R^8)_2$, or $R^9OC(O)NR^8$—, and
  c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, $R^8OC(O)$—, —$N(R^8)_2$, or $R^9OC(O)NR^8$—;
$R^7$ is selected from: hydrogen and $C_1$–$C_6$ alkyl;
$R^8$ is independently selected from hydrogen, $C_1$–$C_6$ alkyl, benzyl and aryl;
$R^9$ is independently selected from $C_1$–$C_6$ alkyl and aryl;
$A^1$ and $A^2$ are independently selected from: a bond, —CH=CH—, —C≡C—, —C(O)—, —C(O)$NR^8$—, O, —$N(R^8)$—, or $S(O)_m$;
$A^3$ is selected from: —$NR^5C(O)$— or —C(O)NH—;
V is selected from:
  a) heterocycle selected from pyrrolidinyl, imidazolyl, pyridinyl, thiazolyl, pyridonyl, 2-oxopiperidinyl, indolyl, quinolinyl, isoquinolinyl, and thienyl,
  b) aryl,
  c) $C_1$–$C_{20}$ alkyl wherein from 0 to 4 carbon atoms are replaced with a heteroatom selected from O, S, and N, and
  d) $C_2$–$C_{20}$ alkenyl, and
W is a heterocycle selected from pyrrolidinyl, pyridinyl, thiazolyl, pyridonyl, 2-oxopiperidinyl, indolyl, quinolinyl, or isoquinolinyl;

m is 0, 1 or 2;

n is 0, 1, 2, 3 or 4;

p is 0, 1, 2, 3 or 4;

r is 0 to 5; and t is 1;

or an optical isomer or pharmaceutically acceptable salt thereof.

3. The compound according to claim 1 of the formula Ic:

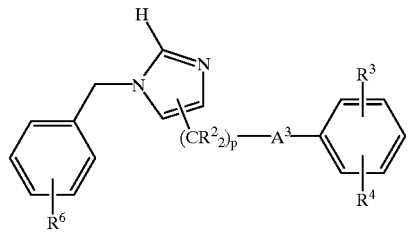

wherein:

$R^{1b}$ is independently selected from:
a) hydrogen,
b) aryl, heterocycle, cycloalkyl, $R^8O$—, —$N(R^8)_2$ or $C_2$–$C_6$ alkenyl,
c) $C_1$–$C_6$ alkyl unsubstituted or substituted by aryl, heterocycle, cycloalkyl, alkenyl, $R^8O$—, or —$N(R^8)_2$;

$R^2$ are independently selected from: hydrogen or $C_1$–$C_6$ alkyl;

$R^3$ and $R^4$ are independently selected from: hydrogen, perfluoroalkyl, F, Cl, Br, $R^8O$—, $R^9S(O)_m$—, CN, $NO_2$, $R^8_2N$—$C(NR^8)$—, $R^8C(O)$—, $R^8OC(O)$—, $N_3$, —$N(R^8)_2$, or $R^9OC(O)NR^8$— and $C_1$–$C_6$ alkyl;

$R^5$ is selected from:
a) hydrogen, and
b) $C_1$–$C_6$ alkyl substituted with hydrogen or a group selected from unsubstituted or substituted aryl, unsubstituted or substituted heterocyclic, unsubstituted or substituted $C_3$–$C_{10}$ cycloalkyl, $N(R^8)_2$, $CF_3$, $NO_2$, $(R^8)O$—, $(R^9)S(O)_m$—, $(R^8)C(O)NH$—, $H_2N$—$C(NH)$—, $(R^8)C(O)$—, $(R^8)OC(O)$—, $N_3$, CN $(R^9)OC(O)NR^8$—;

$R^6$ is independently selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, $R^8OC(O)$—, —$N(R^8)_2$, or $R^9OC(O)NR^8$—, and
c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, $R^8OC(O)$—, —$N(R^8)_2$, or $R^9OC(O)NR^8$—;

$R^8$ is independently selected from hydrogen, $C_1$–$C_6$ alkyl, benzyl and aryl;

$R^9$ is independently selected from $C_1$–$C_6$ alkyl and aryl;

$A^3$ is selected from: —$NR^5C(O)$— or —$C(O)NH$—;

m is 0, 1 or 2; and p is 0, 1, 2, 3 or 4;

or an optical isomer or pharmaceutically acceptable salt thereof.

4. The compound according to claim 1 of the formula Id:

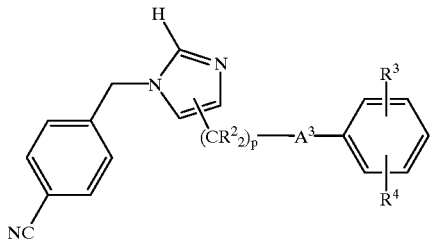

wherein:

$R^{1b}$ is independently selected from:
a) hydrogen,
b) aryl, heterocycle, cycloalkyl, $R^8O$—, —$N(R^8)_2$ or $C_2$–$C_6$ alkenyl,
c) $C_1$–$C_6$ alkyl unsubstituted or substituted by aryl, heterocycle, cycloalkyl, alkenyl, $R^8O$—, or —$N(R^8)_2$;

$R^2$ are independently selected from: hydrogen or $C_1$–$C_6$ alkyl;

$R^3$ and $R^4$ are independently selected from: hydrogen, perfluoroalkyl, F, Cl, Br, $R^8O$—, $R^9S(O)_m$—, CN, $NO_2$, $R^8_2N$—$C(NR^8)$—, $R^8C(O)$—, $R^8OC(O)$—, $N_3$, —$N(R^8)_2$, or $R^9OC(O)NR^8$— and $C_1$–$C_6$ alkyl;

$R^5$ is selected from:
a) hydrogen, and
b) $C_1$–$C_6$ alkyl substituted with hydrogen or a group selected from unsubstituted or substituted aryl, unsubstituted or substituted heterocyclic, unsubstituted or substituted $C_3$–$C_{10}$ cycloalkyl, $N(R^8)_2$, $CF_3$, $NO_2$, $(R^8)O$—, $(R^9)S(O)_m$—, $(R^8)C(O)NH$—, $H_2N$—$C(NH)$—, $(R^8)C(O)$—, $(R^8)OC(O)$—, $N_3$, CN $(R^9)OC(O)NR^8$—;

$R^8$ is independently selected from hydrogen, $C_1$–$C_6$ alkyl, benzyl and aryl;

$R^9$ is independently selected from $C_1$–$C_6$ alkyl and aryl;

$A^3$ is selected from: —$NR^5C(O)$— or —$C(O)NH$—;

m is 0, 1, or 2; and p is 0, 1, 2, 3 or 4;

or an optical isomer or pharmaceutically acceptable salt thereof.

5. A compound which inhibits farnesyl-protein transferase which is:

N-(3-chlorophenyl)-3-[1-(4-cyanobenzyl)-5-imidazolyl] propionamide hydrochloride (1)

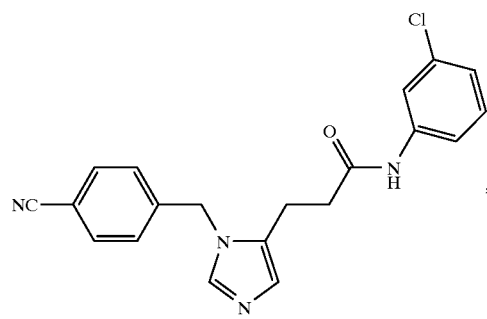

or a pharmaceutically acceptable salt thereof.

6. A pharmaceutical composition comprising a pharmaceutical carrier, and dispersed therein, a therapeutically effective amount of a compound of claim 1.

7. A pharmaceutical composition comprising a pharmaceutical carrier, and dispersed therein, a therapeutically effective amount of a compound of claim 2.

8. A pharmaceutical composition comprising a pharmaceutical carrier, and dispersed therein, a therapeutically effective amount of a compound of claim 6.

9. A method for inhibiting farnesyl-protein transferase which comprises administering to a mammal in need thereof a therapeutically effective amount of a composition of claim 8.

10. A method for treating cancer, wherein the cancer is selected from colorectal carcinoma, exocrine pancreatic carcinoma, myeloid leukemias and neurological tumors, which comprises administering to a mammal in need thereof a therapeutically effective amount of a composition of claim 8.

11. A method for treating neurofibromen benign proliferative disorder which comprises administering to a mammal in need thereof a therapeutically effective amount of a composition of claim 6.

12. A method for treating blindness related to retinal vascularization which comprises administering to a mammal in need thereof a therapeutically effective amount of a composition of claim 6.

13. A method for treating infections from hepatitis delta and related viruses which comprises administering to a mammal in need thereof a therapeutically effective amount of a composition of claim 6.

14. A method for preventing restenosis which comprises administering to a mammal in need thereof a therapeutically effective amount of a composition of claim 6.

15. A method for treating polycystic kidney disease which comprises administering to a mammal in need thereof a therapeutically effective amount of a composition of claim 6.

* * * * *